United States Patent [19]
Taube et al.

[11] Patent Number: 6,127,590
[45] Date of Patent: Oct. 3, 2000

[54] OXIDATIVE COUPLING OF OLEFINS AND AROMATICS USING A RHODIUM CATALYST AND A COPPER(II) REDOX AGENT

[75] Inventors: Douglas Taube, Hayward; Roy Periana, Los Altos; Takaya Matsumoto, Mountain View, all of Calif.

[73] Assignee: Nippon Mitsubishi Oil Corporation, Tokyo, Japan

[21] Appl. No.: 09/277,327

[22] Filed: Mar. 26, 1999

[51] Int. Cl.[7] .............................. C07C 15/46; C07C 1/36; C07C 1/207; C07C 15/40; C07G 1/20
[52] U.S. Cl. ...................... 585/438; 585/435; 585/436; 585/437
[58] Field of Search .................................. 585/435, 436, 585/437, 438

[56] References Cited

U.S. PATENT DOCUMENTS 3,775,511  11/1973  Shue ..................................... 260/669 R
3,848,010  11/1974  Intille ................................... 360/668 R
3,936,473  2/1976  Symon et al. .................... 260/343.2 R

*Primary Examiner*—Marian C. Knode
*Assistant Examiner*—Thuan Dang
*Attorney, Agent, or Firm*—Morrison & Foerster LLP

[57] ABSTRACT

This invention relates generally to the field of chemical synthesis, and more specifically, to the field of oxidative coupling of olefinic compounds and aromatic compounds, to produce olefinically substituted aromatic compounds. More particularly, this invention relates to methods for oxidative coupling of olefinic compounds and aromatic compounds which employ a rhodium(III) acetylacetonate catalyst and a copper(II) redox agent in a reaction medium which does not comprise a carboxylic acid component. In one embodiment, this invention pertains to methods for the preparation of styrene by the oxidative coupling of ethylene (an olefinic compound) and benzene (an aromatic compound), in the presence of $Rh(acac)_2Cl(H_2O)$, as catalyst, and $Cu(II)(CH_3COO)_2$, as copper(II) redox agent, in which benzene is both a reactant and the reaction medium.

37 Claims, No Drawings

OXIDATIVE COUPLING OF OLEFINS AND AROMATICS USING A RHODIUM CATALYST AND A COPPER(II) REDOX AGENT

FIELD OF THE INVENTION

This invention relates generally to the field of chemical synthesis, and more specifically, to the field of oxidative coupling of olefinic compounds and aromatic compounds, to produce olefinically substituted aromatic compounds. More particularly, this invention relates to methods for oxidative coupling of olefinic compounds and aromatic compounds which employ a rhodium(III) acetylacetonate catalyst and a copper(II) redox agent in a carboxylic acid-free reaction medium. In one embodiment, this invention pertains to methods for the preparation of styrene by the oxidative coupling of ethylene (an olefinic compound) and benzene (an aromatic compound), in the presence of $Rh(acac)_2Cl_1(H_2O)$, as catalyst, and Cu(II) acetate, as copper(II) redox agent, in which benzene is both a reactant and the reaction medium.

BACKGROUND

Throughout this application, various publications, patents, and published patent applications are referred to by an identifying citation; full citations for these documents may be found at the end of the specification immediately preceding the claims. The disclosures of the publications, patents, and published patent specifications referenced in this application are hereby incorporated by reference into the present disclosure to more fully describe the state of the art to which this invention pertains.

The oxidative coupling of olefinic compounds and aromatic compounds, to produce olefinically substituted aromatic compounds, is well known, and may be simplistically represented by the following reaction:

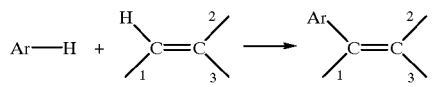

A common example of oxidation coupling is the reaction of ethylene and benzene, to produce styrene, as shown below.

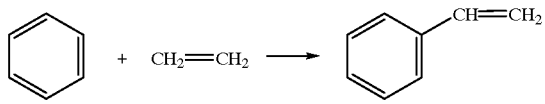

The direct oxidative coupling of olefinic compounds and aromatic compounds in the presence of both stoichiometric and catalytic quantities of Group VIII metal salts has been demonstrated in the prior art. See, for example, Shue, 1973, and Intille, 1974. In this context, the Group VIII metals are iron, cobalt, nickel, ruthenium, rhodium, palladium, osmium, iridium, and platinum. Heretofore, the most preferred Group VIII metal has been palladium(II), usually provided in the form of a palladium carboxylate, for example, as palladium(II) acetate.

In non-catalytic direct oxidative coupling of olefinic compounds and aromatic compounds, a stoichiometric quantity of the Group VIII metal, as oxidant, is required. During the reaction, the Group VIII metal is reduced and rendered unreactive towards the coupling reaction. In many cases, the reaction can be made catalytic with respect to the Group VIII metal by the addition of a oxidizing agent, which converts the spent (reduced) Group VIII metal back into a reactive (oxidized) form, thereby regenerating the catalyst. Examples of oxidizing agents which have been used in this fashion include iodine, $PbO_2$, $Ag_2O_2$, and Cu(II) salts. If a copper(II) salt is employed, the reaction can further be made catalytic with respect to copper by the introduction of molecular oxygen, which converts spent copper back to copper(II). However, the reaction with molecular oxygen usually requires activation, for example, by a carboxylic acid such as acetic acid, which may be used as the solvent or as a co-solvent.

Despite a possible improvement in reaction rate, the use of a carboxylic acid, such as acetic acid, as a solvent or co-solvent, has several disadvantages. Carboxylic acids are often reactive towards the olefinic compound under the reaction conditions employed, leading to a substantial quantity of undesired by-products. For example, the reaction of benzene and ethylene in the presence of acetic acid typically yields a substantial quantity of vinyl acetate, by the following reaction:

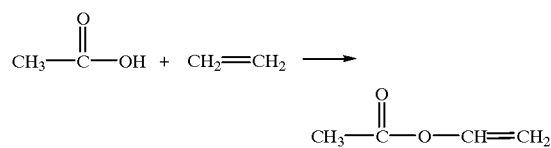

Often twice as much vinyl acetate as styrene is produced in the reaction between benzene and ethylene using a palladium(II) acetate catalyst. This disadvantage has been recognized (see, for example, Shue, 1973) and a solution proposed: use a catalytic amount of palladium carboxylate, a large excess of aromatic compound, in the presence of molecular oxygen at relatively low reaction temperatures (see, for example, col. 7, line 72 through col. 8, line 32 of Shue, 1973).

Applicants have discovered an altogether different solution to the problem. Applicants have discovered that the use of a different catalyst, specifically a rhodium(III) acetylacetonate catalyst in conjunction with a copper(II) redox agent, in a reaction medium which does not comprise a carboxylic acid, results in a comparable catalyst turn over frequency as well as a substantially higher selectivity for the desired product.

SUMMARY OF THE INVENTION

One aspect of the present invention pertains to a process for coupling of an olefinic compound having at least one carbon—carbon double bond and at least one hydrogen atom attached to one of the carbon atoms of said carbon—carbon double bond, and an aromatic compound having aromatic ring atoms and a hydrogen atom covalently attached to at least one of said aromatic ring atoms, which process comprises the step of: reacting said olefinic compound with said aromatic compound in the presence of a rhodium(III) acetylacetonate catalyst and a copper(II) redox agent in a reaction medium which does not comprise a carboxylic acid component.

In one embodiment, the rhodium(III) acetylacetonate catalyst is $Rh(acac)_2Cl(H_2O)$.

In one preferred embodiment, the copper(II) redox agent is $Cu(CH_3COO)_2$ or copper (II) acetate.

In one aspect of the process of the invention, the olefinic compound has from 2 to 12 carbon atoms, and has from zero to two substituents selected from the group consisting of: $C_{1-4}$ alkyl, $C_{3-6}$ cycloalkyl, $C_{6-12}$ aryl, $C_{7-16}$ alkaryl and $C_{7-16}$ aralkyl, wherein each of said substituents may be unsubstituted or may be further substituted with one or more substituents selected from the group consisting of: hydroxy, carboxylic acid, ester, aldehyde, ketone, amide, substituted amide, and nitro. In one preferred embodiment, the olefinic compound is ethylene.

In another aspect of the process of the invention, the aromatic compound has from 6 to 12 carbon atoms, and has from zero to two substituents selected from the group consisting of: $C_{1-4}$ alkyl, $C_{3-6}$ cycloalkyl, $C_{6-12}$ aryl, $C_{7-16}$ alkaryl and $C_{7-16}$ aralkyl, wherein each of said substituents may be unsubstituted or may be further substituted with one or more substituents selected from the group consisting of: hydroxy, carboxylic acid, ester, aldehyde, ketone, amide, substituted amide, and nitro. In one preferred embodiment, the aromatic compound is benzene.

In one preferred aspect of the invention, the aromatic compound is also said reaction medium.

In one embodiment, the reaction is carried out at a temperature of about 150° C. to about 250° C.

Another aspect of the present invention pertains to providing an oxidative coupling method which offers improved selectivity.

Still another aspect of the present invention pertains to providing an oxidative coupling method which offers comparable or improved reaction rate and/or catalyst turn over frequency.

As will become apparent, preferred features and characteristics of one aspect of the invention are applicable to any other aspect of the invention.

DETAILED DESCRIPTION OF THE INVENTION

This invention relates to processes for the coupling of an olefinic compound and an aromatic compound which comprises the step of reacting said olefinic compound with said aromatic compound in the presence of a rhodium(III) acetylacetonate catalyst and a copper(II) redox agent in a reaction medium which does not comprise a carboxylic acid component. For convenience, the reaction may simplistically be represented as shown below:

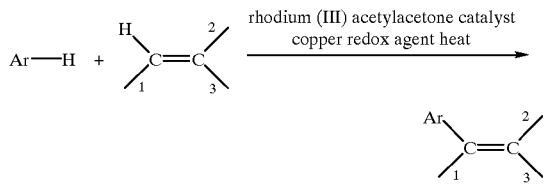

Olefinic Compounds

This invention relates to processes for the coupling of an olefinic compound and an aromatic compound. The term "olefinic compound," as used herein, pertains to an organic compound which possesses at least one carbon—carbon double bond, with the proviso that at least one of the carbon atoms of said carbon—carbon double bond has at least one hydrogen atom attached thereto. If applicable, said carbon—carbon bond may be in either the cis or trans conformation. The term "organic compound" is used herein in the conventional sense, and pertains to chemical compounds which comprise at least one carbon atom in combination with (covalently bound to) one or more other atoms.

Olefinic compounds suitable for use in the present invention may be represented by the following formula wherein H denotes a hydrogen atom covalently attached to one of the carbon atoms of the carbon—carbon double bond, and the bonds marked 1, 2, and 3, link the carbon atoms of the carbon—carbon double bond to other atoms in the compound.

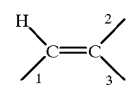

Olefinic compounds may be, or may comprise, linear, branched, or cyclic moieties. In one embodiment, the olefinic compound is linear. In one embodiment, the olefinic compound is branched. In one embodiment, the olefinic compound is cyclic. In one embodiment, the olefinic compound comprises a cyclic group.

In one embodiment, the olefinic compound has from 2 to 20 carbon atoms. In one embodiment, the olefinic compound has from 2 to 10 carbon atoms. In one preferred embodiment, the olefinic compound has from 2 to 8 carbon atoms. In one embodiment, the olefinic compound more preferably has from 2 to 6 carbon atoms; and most preferably from 2 to 4 carbon atoms.

Olefinic compounds may have only one carbon—carbon double bond; such compounds may conveniently be referred to as mono-olefinic compounds. Olefinic compounds may have two or more carbon—carbon double bonds; such compounds may conveniently be referred to as poly-olefinic compounds.

The olefinic compound may further comprise one or more hydrocarbon substituents (i.e., substituents consisting only of carbon and hydrogen) which may be linear, branched, alicyclic, or aromatic, or combinations thereof, and which may be fully saturated, partially unsaturated, or fully unsaturated. Examples of hydrocarbon substituents include, but are not limited to, alkyl (e.g., $C_{1-4}$ alkyl), cycloalkyl (e.g., $C_{3-6}$ cycloalkyl), aryl (e.g., $C_{6-12}$ aryl), alkaryl (e.g., $C_{7-16}$ alkaryl), and aralkyl (e.g., $C_{7-16}$ aralkyl). Examples of alkyl substituents include, but are not limited to, methyl, ethyl, n-propyl, isopropyl, n-butyl, isobutyl, sec-butyl, and tert-butyl. Examples of cycloalkyl substituents include, but are not limited to, cyclopropyl, cyclobutyl, cyclopentyl, and cyclohexyl. Examples of aryl substituents include, but are not limited to, phenyl and naphthyl. Examples of alkaryl substituents include, but are not limited to, 2-methylphen-1-yl (i.e., o-tolyl), 3-methylphen-1-yl (i.e., m-tolyl), 4-methylphen-1-yl (i.e., p-tolyl), 2,3-dimethylphen-1-yl (i.e., 2,3-xylyl), 3,4-dimethylphen-1-yl (i.e., 3,4-xylyl), and 2,4,6-trimethylphen-1 yl (i.e., mesityl). Examples of aralkyl substituents include, but are not limited to, phenylmethyl (i.e., benzyl), phenylethyl (i.e., phenethyl), and triphenylmethyl (i.e., trityl). Examples of unsaturated hydrocarbon substituents include, but are not limited to, vinyl (i.e., —CH═CH$_2$) and allyl (i.e., —CH$_2$CH═CH$_2$).

The olefinic compound, and any hydrocarbon substituents thereon, may further comprise one or more non-hydrocarbon substituents, which comprise at least one atom other than carbon and hydrogen, including, but not limited to, oxygen, sulfur, nitrogen, phosphorus, fluorine, chlorine, bromine, and iodine. Examples of non-hydrocarbon substituents include, but are not limited to, halogen groups (e.g., —F, —Cl, —Br, —I), hydroxy group (i.e., —OH), ether groups (e.g., —OR), carboxylic acid group (i.e., —COOH), ester groups (e.g., —COOR), aldehyde group (i.e., —CHO), ketone groups (e.g., —C(=O)R), amide group (i.e., —C(=O)NH$_2$), substituted amide groups (e.g., —C(=O)NR$_2$), amino group (i.e., —NH$_2$), substituted amino groups (e.g., —NHR, —NR$_2$), nitro group (i.e., —NO$_2$), nitroso group (i.e., —NO), cyano group (i.e., —CN), cyanato group (i.e., —OCN), isocyanato group (i.e., —NCO), thiocyanato group (i.e., —SCN), isothiocyanato group (i.e., —NCS), thiol group (i.e., —SH), thioether groups (e.g., —SR), sulfonate group (i.e., —SO$_3$H), and halogenated alkyl groups (e.g., —CF$_3$). Preferably, non-hydrocarbon substituents of the olefinic compounds do not act, or do not substantially act, as poisons for the rhodium(III) acetylacetonate catalyst described below, or lead or substantially lead to undesired cross-reactions or side-reactions.

In one embodiment, the olefinic compound has from 2 to 12 carbon atoms, and has from zero to two substituents selected from the group consisting of alkyl (e.g., $C_{1-4}$ alkyl), cycloalkyl (e.g., $C_{3-6}$ cycloalkyl), aryl (e.g., $C_{6-12}$ aryl), alkaryl (e.g., $C_{7-16}$ alkaryl), and aralkyl (e.g., $C_{7-16}$ aralkyl), each of which may be unsubstituted or substituted with one or more substituents selected from the group consisting of hydroxy group (i.e., —OH), carboxylic acid group (i.e., —COOH), ester groups (e.g., —COOR), aldehyde group (i.e., —CHO), ketone groups (e.g., —C(=O)R), amide group (i.e., —C(=O)NH$_2$), substituted amide groups (e.g., —C(=O)NR$_2$), and nitro group (i.e., —NO$_2$).

Examples of olefinic compounds, which are linear mono-olefinic hydrocarbons, include, but are not limited to: ethene, also known as ethylene; propene, also known as propylene; 1-butene or 2-butene; the linear pentenes (e.g., 1-pentene; 2-pentene); the linear hexenes (e.g., 1-hexene; 2-hexene; 3-hexene); the linear heptenes (e.g., 1-heptene), the linear octenes (e.g., 1-octene); the linear nonenes (e.g., 1-nonene); the linear decenes (e.g., 1-decene); the linear dodecenes (e.g., 1-dodecene); and the linear eicosenses (e.g., 1-eicosene).

Examples of olefinic compounds, which are branched mono-olefinic hydrocarbons include, but are not limited to: 2-methylpropene (also known as isobutene and isobutylene); 2-methyl-1-butene; 3-methyl-1-butene; 2,3,3,-trimethyl-1-butene, also known as triptene; and 2-methyl-2-butene.

Examples of olefinic compounds, which are cyclic mono-olefinic hydrocarbons include, but are not limited to, cyclopentene, methylcyclopentene, cyclohexene, 1-methylcyclohexene, 3-methylcyclohexene, 1,2-dimethylcyclohexene, and cyclooctene.

Examples of olefinic compounds, which are poly-olefinic hydrocarbons include, but are not limited to: 1,2-butadiene, also known as methylallene; 1,3-butadiene, also known as bivinyl; 1,3-pentadiene, 1,5-heptadiene, divinyl benzene, vinylcyclohexene, and allylcyclohexene.

Examples of olefinic compounds, which comprise a heteroatom, include but are not limited to, vinyl chloride, vinyl fluoride, vinylidene chloride, allyl bromide, chlorostyrene, trichloroethylene, acrylic acid, crotonic acid, maleic acid, ethyl maleate, p-vinyl benzoic acid, vinyl acetate, allyl proprionate, propenyl acetate, butenyl caproate, ethylidene diacetate. methyl acrylate, and methyl methacrylate.

In one preferred embodiment, the olefinic compound is selected from the group consisting of ethylene and propylene. Most preferably, the Olefinic compound is ethylene.

In one embodiment, the olefinic compound is ethylene.

Aromatic Compounds

This invention relates to processes for the coupling of an olefinic compound and an aromatic compound. The term "aromatic compound" is used herein in the conventional sense and refers to organic compounds which are characterized by one or more cyclic aromatic structures, that is, cyclic structures having delocalized pi-electron orbitals. The atoms which form the cyclic aromatic structure may conveniently be identified as aromatic ring atoms. Aromatic compounds may have a single cyclic aromatic structure (and may be conveniently referred to as "monoaromatic"), as in benzene. Alternatively, aromatic compounds may have more than one cyclic aromatic structure (and may be conveniently referred to as "polyaromatic"): some or all of these structures may be linked by one or more non-aromatic groups which separate their aromatic structures (as in, for example, benzyl benzene, $C_6H_5$—$CH_2$—$C_6H_5$), or they may be fused together (and may be conveniently referred to as "fused polyaromatic") so as to join their aromatic structures, as in, for example, naphthalene, $C_{10}H_8$. Aromatic compounds may consist only of carbon and hydrogen atoms (and may be conveniently referred to as "aromatic hydrocarbons") or they may have one or more heteroatoms (e.g., oxygen, sulfur, nitrogen, phosphorus, halogen).

Aromatic compounds which are suitable for use in the present invention are organic compounds which are characterized by one or more cyclic aromatic structures having aromatic ring atoms, with the proviso that at least one of said aromatic ring atoms has a hydrogen atom covalently attached thereto. In one embodiment, at least one of said aromatic ring atoms is a carbon atom, and said aromatic ring carbon atom has a hydrogen atom covalently attached thereto.

Aromatic compounds suitable for use in the present invention may be represented by the formula HAr, wherein Ar denotes a chemical moiety comprising at least one cyclic aromatic structure having aromatic ring atoms, and H denotes a hydrogen atom covalently attached to one of said aromatic ring atoms.

In one embodiment, the aromatic compound suitably has from 6 to 20 carbon atoms. In one preferred embodiment, the aromatic compound has from 6 to 15 carbon atoms. In one embodiment, the aromatic compound more preferably has from 6 to 12 carbon atoms and most, preferably, the aromatic compound has from 6 to 8 carbon atoms. In one embodiment, the aromatic compound comprises only carbon ring atoms. In one embodiment, the aromatic compound comprises one or more ring heteroatoms (e.g., oxygen, nitrogen, sulfur).

The aromatic compound may further comprise one or more hydrocarbon substituents (i.e., substituents consisting only of carbon and hydrogen) which may be linear, branched, alicyclic, or aromatic, or combinations thereof, and which may be fully saturated, partially unsaturated, or fully unsaturated. Examples of hydrocarbon substituents include, but not limited to, alkyl (e.g., $C_{1-4}$ alkyl), cycloalkyl (e.g., $C_{3-6}$ cycloalkyl), aryl (e.g., $C_{6-12}$ aryl), alkaryl (e.g., $C_{7-16}$ alkaryl), and aralkyl (e.g., $C_{7-16}$ aralkyl). Examples of alkyl substituents include, but are not limited to, methyl, ethyl, n-propyl, isopropyl, n-butyl, isobutyl, sec-butyl, and tert-butyl. Examples of cycloalkyl substituents include, but are not limited to, cyclopropyl, cyclobutyl, cyclopentyl, and cyclohexyl. Examples of aryl substituents include, but are not limited to, phenyl and naphthyl. Examples of alkaryl substituents include, but are not limited to, 2-methylphen-1-yl (i.e., o-tolyl), 3-methylphen-1-yl (i.e., m-tolyl), 4-methylphen-1-yl (i.e., p-tolyl), 2,3-dimethylphen-1-yl (i.e., 2,3-xylyl), 3,4-dimethylphen-1-yl (i.e., 3,4-xylyl), and 2,4,6-trimethylphen-1yl (i.e., mesityl). Examples of aralkyl substituents include, but are not limited to, phenylmethyl (i.e., benzyl), phenylethyl (i.e., phenethyl), and triphenylmethyl (i.e., trityl). Examples of unsaturated hydrocarbon substituents include, but are not limited to, vinyl (i.e., —CH=CH$_2$) and allyl (i.e., —CH$_2$—Cl=CH$_2$).

The aromatic compound, and any hydrocarbon substituents thereon, may further comprise one or more non-hydrocarbon substituents, which comprise at least one atom other than carbon and hydrogen, including, but not limited to, oxygen, sulfur, nitrogen, phosphorus, fluorine, chlorine, bromine, and iodine. Examples of non-hydrocarbon substituents include, but not limited to, halogen groups (e.g., —F, —Cl, —Br, —I), hydroxy group (i.e., —OH), ether groups (e.g., —OR), carboxylic acid group (i.e., —COOH), ester groups (e.g., —COOR), aldehyde group (i.e., —CHO), ketone groups (e.g., —C(=O)R), amide group (i.e., —C(=O)NH$_2$), substituted amide groups (e.g., —C(=O)NR$_2$), amino group (i.e., —NH$_2$), substitued amino groups (e.g., —NHR, —NR$_2$), nitro group (i.e., —NO$_2$), nitroso group (i.e., —NO), cyano group (i.e., —CN), cyanato group (i.e., —OCN), isocyanato group (i.e., —NCO), thiocyanato group (i.e., —SCN), isothiocyanato group (i.e., —NCS), thiol group (i.e., —SH), thioether groups (e.g., —SR), sulfonate group (i.e., —SO$_3$H), and halogenated alkyl groups (e.g., —CF$_3$). Preferably, non-hydrocarbon substituents of the aromatic compounds do not act, or do not substantially act, as poisons for the rhodium(III) acetylacetonate catalyst described below, nor do they lead or substantially lead to undesired cross-reactions or side-reactions.

In one embodiment, the aromatic compound is a liquid at the temperature of the reaction, as discussed below. In one embodiment, the aromatic compound is a liquid or a solid which melts at a temperature of about 200° C. or lower, more preferably about 175° C. or lower, more preferably about 150° C. or lower. In this way, in one embodiment, the aromatic compound itself may be used as the reaction medium.

In one embodiment, the aromatic compound has from 6 to 12 carbon atoms, and has from zero to two substituents selected from the group consisting of alkyl (e.g., C$_{1-4}$ alkyl), cycloalkyl (e.g., C$_{3-6}$ cycloalkyl), aryl (e.g., C$_{6-12}$ aryl), alkaryl (e.g., C$_{7-16}$ alkaryl), and aralkyl (e.g, C$_{7-16}$ aralkyl), each of which may be unsubstituted or substituted with one or more substituents selected from the group consisting of hydroxy group (i.e., —OH), carboxylic acid group (i.e., —COOH), ester groups (e.g., —COOR), aldehyde group (i.e., —CHO), ketone groups (e.g., —C(=O)R), amide group (i.e., —C(=O)NH$_2$), substituted amide groups (e.g., —C(=O)NR$_2$), and nitro group (i.e., —NO$_2$).

Examples of aromatic compounds, which are monoaromatic hydrocarbons, include, but are not limited to, benzene, methylbenzene (i.e., toluene), 1,2-dimethylbenzene (i.e., o-xylene), 1,3-dimethylbenzene (i.e., m-xylene), 1,4-dimethylbenzene (i.e., p-xylene), 1,3,5-trimethylbenzene (i.e., mesitylene), 1,2,3-trimethylbenzene, 1,2,4-trimethylbenzene, tetramethylbenzene, pentamethylbenzene, ethylbenzene, n-propylbenzene, isopropylbenzene (i.e., cumene), 1-isopropyl-4-methylbenzene (i.e., p-cymine), n-butylbenzene, 2-butylbenzene, isobutylbenzene, tert-butylbenzene, n-pentylbenzene, cyclopentylbenzene, neopentylbenzene, cyclohexylbenzene, 1-cyclohexyl-4-methylbenzene, cyclooctylbenzene, styrene, methylvinylbenzene, and divinylbenzene.

Examples of aromatic compounds, which are polyaromatic hydrocarbons, include, but are not limited to, biphenyl, biphenylene, terphenyl, naphthalene, azulene, anthracene, phenanthrene, triphenylene, pyrene, 2,2'-dimethylbiphenyl, diphenylmethane, 1,2-diphenylethane, and 1,8-diphenyloctane.

Examples of aromatic compounds, which comprise a heteroatom (either as a ring atom or as, or as part of, a substituent), include but are not limited to, methoxybenzene (i.e., anisole), ethoxybenzene, nitrobenzene, methyl benzoate, ethyl benzoate, isobutyl benzoate, diphenyl ether, cyclohexylphenyl ether, benzonitrile, phenyl acetate, phenyl hexanoate, tolyl acetate, phenol, benzaldehyde, acetophenone, chlorobenzene, 2-chloroxylene, bromobenzene, trichlorobenzene, 1,4-dichlorobenzene, and 1,2-dibromonaphthalene.

In one embodiment, the aromatic compound is selected from the group consisting of benzene, methylbenzene (i.e., toluene), 1,2-dimethylbenzene (i.e., o-xylene), 1,3-dimethylbenzene (i.e., m-xylene), 1,4-dimethylbenzene (i.e., p-xylene), methylethylbenzene, methylvinylbenzene, styrene, and divinylbenzene.

In one embodiment, the aromatic compound most preferably is benzene.

Rhodium(III) Acetylacetonate Catalyst

The coupling reaction of the present invention is performed in the presence of a rhodium(III) acetylacetonate catalyst. The term "rhodium(III) acetylacetonate," as used herein, pertains to a chemical compound comprising at least one rhodium atom in the +3 oxidation state, and at least one acetylacetonate group. In one embodiment, the rhodium(III) acetylacetonate catalyst has only one rhodium atom.

The term "acetylacetonate group" (often referred to by the acronym "acac") is used herein in the conventional sense to refer to the anion obtained by deprotonation of the enol tautomer of acetylacetone.

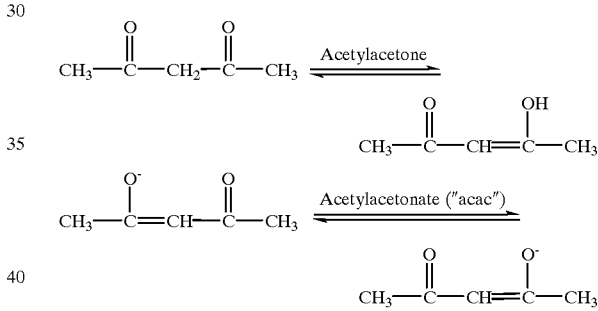

Acetylacetonate typically acts as a bidentate anion ligand, bonding via the oxygen atom of each of the carbonyl groups.

A number of rhodium(III) compounds are commercially available, including rhodium(III) chloride (i.e., RhCl$_3$), rhodium(III) chloride hydrate (i.e., RhCl$_3$∃xH$_2$O), rhodium (III) bromide hydrate (i.e., RhBr$_3$∃xH$_2$O), and rhodium(III) iodide hydrate (i.e., RhI$_3$∃xH$_2$O). In aqueous solution, these trihalides typically form solvated hexa-coordinate species, for example, RhCl$_3$(H$_2$O)$_3$, RhBr$_3$(H$_2$O)$_3$, and RhI$_3$(H$_2$O)$_3$. Further reaction of these species, for example, with sodium acetylacetonate (i.e., Na(acac)) typically yields rhodium(III) acetylacetonate species which possess from one to three acac groups and which are useful as rhodium(III) acetylacetonate catalysts in the present invention.

In one embodiment, the rhodium(III) acctylacetonate catalyst has one acac group. Examples of such species include, but are not limited to, Rh(acac)Cl$_3$(H$_2$O) Rh(acac) Cl$_2$(H$_2$O)$_2$, Rh(acac)Cl(H$_2$O)$_3$, Rh(acac)Br$_3$(H$_2$O), Rh(acac)Br$_2$(H$_2$O)$_2$, Rh(acac)Br(H$_2$O)$_3$, Rh(acac)I$_3$(H$_2$O), Rh(acac)I$_2$(H$_2$O)$_2$, and Rh(acac)I(H$_2$O)$_3$.

In one embodiment, the rhodium(III) acetylacetonate catalyst has two acac groups. Examples of such species include, but are not limited to, Rh(acac)$_2$Cl(H$_2$O), Rh(acac)$_2$Cl$_2$, Rh(acac)$_2$Br(H$_2$O), Rh(acac)$_2$Br$_2$, Rh(acac)$_2$I(H$_2$O), Rh(acac)$_2$I$_2$, and Rh(acac)$_2$(H$_2$O)$_2$.

In one embodiment, the rhodium(III) acetylacetonate catalyst has at least one halide atom (e.g., Cl, Br, I).

In one embodiment, the rhodium(III) acetylacetonate catalyst is $Rh(acac)_2Cl(H_2O)$.

Copper(II) Redox Agent

During the oxidation coupling reaction, the rhodium(III) of the rhodium(III) acetylacetonate catalyst is reduced, typically to a rhodium(I) state. In order for the reaction to be catalytic with respect to rhodium, it is necessary to oxidize the rhodium(I) back to rhodium (III), and so regenerate the catalyst. In the present invention, this oxidation achieved using a copper(II) redox agent. The term "copper(II) redox agent," as used herein, pertains to a chemical compound comprising at least one copper atom in the +2 oxidation state. In one embodiment, the copper(II) redox agent has only one copper atom.

In one embodiment, the copper(II) redox agent is a copper(II) salt. In one embodiment, the copper(II) redox agent is a copper(II) inorganic salt, that is, a salt in which the anion or anions are inorganic species. In one embodiment, the copper(II) redox agent is copper(II) chloride (i.e., $CuCl_2$). In one preferred embodiment, the copper(II) redox agent is a copper(II) organic salt, that is, a salt in which the anion or anions are organic species. In one embodiment, the copper(II) redox agent most preferably is copper(II) acetate (i.e., $Cu(CH_3COO)_2$).

Reaction Medium

The coupling reaction of the present invention is performed in a reaction medium which does not comprise or contain a carboxylic acid component.

The term "reaction medium" is used herein in the conventional sense, and relates to the liquid medium in which the olefinic compound and the aromatic compound react to yield the desired product.

The term "carboxylic acid component" is used herein in the conventional sense, and relates to compounds which may be represented by the formula $RC(=O)OH$. Examples of carboxylic acids, which, in the prior art, have been used as a component (i.e., as a solvent or co-solvent) of oxidative coupling reaction media, are acetic acid (i.e., $CH_3C(=O)OH$), propionic acid (i.e., $CH_3CH_2C(=O)OH$), and butyric acid (i.e., $CH_3CH_2CH_2C(=O)OH$).

The reaction may be carried out using the neat reactants or using solutions or dispersions of the reactants. Many of the possible reactants, such as benzene, toluene, xylene, ethylbenzene, phenol, and others will be liquid at the reaction temperature, and may act both as a reactant and as a solvent for the reaction mixture. For example, in the reaction of benzene with ethylene in accordance with a most preferred aspect of this invention, benzene which is present in a large stoichiometric excess acts both as a reactant and as the reaction medium.

If a neat mixture of the olefinic compound and the organic compound do not dissolve or substantially dissolve the rhodium(III) acetylacetonate catalyst, it may be desirable and/or necessary to add a solvent (or co-solvent) in order to dissolve the catalyst.

Some of the possible reactants, such as highly substituted compounds and fused aromatic compounds may be solid at the reaction temperature will typically require a solvent or solvents for the reaction.

Preferred solvents are: (a) solvents other than carboxylic acids, (b) solvents which do not interfere or substantially interfere with the reaction, (c) solvents which do not react or do not substantially react with the reactants or products, and (d) solvents in which the rhodium(II) acetylacetonate catalyst and copper(II) redox agent are soluble or substantially soluble. Solvents which may be suitable, according to the choice of olefinic compound and aromatic compound, include, but are not limited to, water, alcohols (e.g., methanol, ethanol, propanol), sulfones (e.g., methylethylsulfone, diisopropylsulfone), sulfoxides (e.g., dimethylsulfoxide, ethylpropylsulfoxide), amides (e.g., formamide, dimethylformamide, N-methylpyrrolidone, acetamide), ketones (e.g., methylethylketone, acetone, diethylketone), ethers (e.g., diethylether, diisopropylether), hydrocarbons (e.g., cyclohexane, isooctane, methylcyclohexane), and aromatic hydrocarbons (e.g., benzene).

In one preferred embodiment, the reaction is carried out neat, without a solvent. In one embodiment, the reaction is more preferably carried out neat, without a solvent, with a stoichiometric excess of the aromatic compound, which acts both as reactant and solvent (reaction medium).

Reaction Conditions

This invention relates to processes for the coupling of an olefinic compound and an aromatic compound which comprises the step of reacting said olefinic compound with said aromatic compound in the presence of a rhodium(III) acetylacetonate catalyst and a copper(II) redox agent in a reaction medium which does not comprise a carboxylic acid component.

The reaction is carried out using an apparatus which is appropriate for the selected olefinic compound and aromatic compound. For example, when the aromatic compound is a liquid at the reaction temperature and the olefinic compound is a gas at the reaction temperature, as is the case for benzene/ethylene, then a pressure reactor may be most appropriate. When both the aromatic compound and the olefinic compound are liquids at the reaction temperature, then a heated reaction vessel, reflux apparatus, or other apparatus may be most appropriate.

The precise proportions of aromatic compound, olefinic compound, rhodium(III) acetylacetonate catalyst, and copper(II) redox agent may be readily adjusted by one of ordinary skill in the relevant art in order to optimize reaction parameters, for example, catalyst turn over frequency, selectivity, and yield.

The molar ratio of the aromatic compound to the olefinic compound may vary over a wide range. A suitable molar ratio of aromatic compound to olefinic compound is from 0.1:1 to 1000:1. It is normally desired to use a molar ratio of aromatic compound to olefinic compound of more than 1:1 (i.e., a stoichiometric excess of aromatic compound) since the aromatic compound can often be the reaction medium as well as a reactant. It is typically preferable to use a molar ratio of aromatic compound to olefinic compound of from about 10:1 to 100:1, since in this range, olefin—olefin coupling is rendered less significant yet the relative amount of aromatic compound is not so large that recovery of products is hampered.

The molar ratio of the olefinic compound to the rhodium (III) acetylacetonate catalyst may vary over a wide range. Normally, a molar ratio greater than 1:1 will be employed in order to take advantage of the catalytic effect. At low molar ratios of olefinic compound to rhodium(III) acetylacetonate catalyst, olefin—olefin coupling becomes more significant. At very high molar ratios olefinic compound to rhodium(III) acetylacetonate catalyst, the reaction becomes too slow to be practical. In one embodiment, the molar ratio of olefinic compound to rhodium(III) acetylacetonate catalyst is from about 10:1 to about 100:1.

In one preferred embodiment, the aromatic compound serves both as a reactant and as the reaction medium, and so is present in large stoichiometric excess in relation to the olefinic compound.

When the olefinic compound is a gas at the reaction temperature, it may introduced by bubbling it through the reaction mixture, or it may be charged under pressure to a pressure reactor, typically at a partial pressure of from about 1 atm to about 30 atm.

The reaction temperature may be controlled using any suitable apparatus, including, but not limited to, a hot oil bath, a hot water bath, a hot plate, and heating tape. The reaction temperature is typically from about 30° C. to about 300° C. In one preferred embodiment, the reaction temperature is from about 150° C. to about 250° C. In one embodiment, the reaction temperature is more preferably from about 150° C. to about 225° C., and most preferably, the reaction temperature is from about 175° C. to about 225° C.

The reaction can be conducted for a period of time sufficient to cause complete conversion of the starting olefinic compound. However, as the reaction progresses and the concentration of products increases, undesired side reactions, such as polyarylation, become important. Therefore it may be desirable to interrupt the reaction at a time when conversion of the starting olefinic compound is not complete in order to optimize the yield of the desired product. The optimum time will depend upon the nature of the reactants and the operating conditions chosen, such as temperature, mole ratios of the reactants, and like. The selection of an optimum reaction time is within the skill of one experienced in the relevant art. One manner in which it can be done is to examine aliquots, taken periodically from the reaction, by vapor phase chromatography or other suitable technique. By observing the nature of the product mixture as it varies with time, the time at which maximization of the desired product occurs (relative to unreacted starting material and undesired byproducts) can be determined. The reaction time is typically from about 1 minute to 24 hours. In one embodiment, the reaction time is from about 10 minutes to about 6 hours. In one embodiment, the reaction time is from about 10 minutes to about 2 hours.

It may also be desirable to carry out the reaction in the presence of molecular oxygen, which may be introduced by bubbling it through the reaction mixture, or it may be charged under pressure to a pressure reactor, typically at a partial pressure of from about 1 atm to about 30 atm.

EXAMPLES

The present invention is illustrated in the following examples, which are not intended to limit the scope of the invention as set forth in the appended claims.

Example 1

Preparation of a Rhodium(II) Acetylacetonate Catalyst $RhCl_3(H_2O)_3$ (810 mg, 3.112 mmoles) was added to Na(acac) (760 mg, 6.231 mmoles) along with 40 mL distilled water and the mixture refluxed for 3 hours under nitrogen. The resultant solution was evaporated to dryness giving a red-brick solid. The red solid was dissolved in a 50/50 (v/v) mixture of ethanol and chloroform and filtered, leaving behind a white solid (NaCl). The solution was evaporated to dryness and chromatographed on $SiO_2$ using chloroform as the initial eluent and slowly increasing the amount of ethanol to elute the red bands. Five fractions were collected. The bands were collected and evaporated to dryness. Tests showed that the second through fifth bands had nearly identical activity towards styrene production from benzene and ethylene. $^1H$ and $^{13}C$ NMR spectra and elemental analysis were performed and the results were consistent with the formation of $Rh(acac)_2Cl(H_2O)$.

Example 2

Formation of Styrene from Benzene and Ethylene

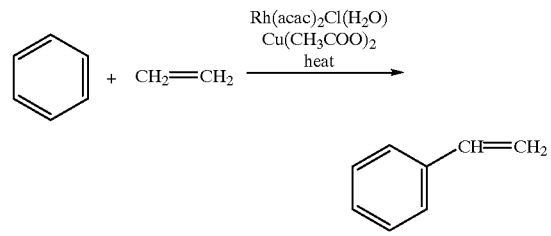

$Rh(acac)_2Cl(H_2O)$ (2 mg, $5.6 \times 10^{-6}$ moles) was added to a glass vial containing a Teflon coated magnetic stirbar. Copper(II) acetate (400 mg, $2.2 \times 10^{-3}$ moles) was also added along with 2 mL of benzene. The vial was placed inside a pressure reactor where the system was purged with nitrogen, and then filled to 300 psig (about 21 atm) with ethylene. The mixture was stirred and heated to 200° C. for 1 hour, after which the reactor was cooled and vented. The solution, which was originally a blue-slurry, had become a greenish-brown following the reaction. The solution was centrifuged and analyzed by gas chromatography. The solution contained styrene (114 mM, $2.2 \times 10^{-4}$ moles) and a small amount (6 mM) of vinyl acetate.

Example 3

Formation of Styrene from Benzene and Ethylene (Not according to the Invention)

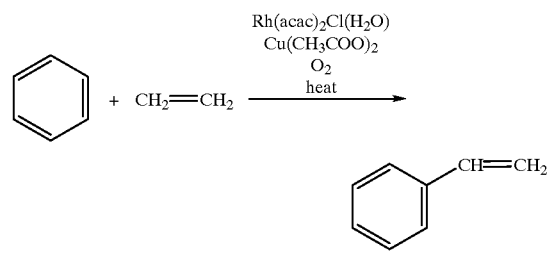

$Rh(acac)_2Cl(H_2O)$ (2.2 mg, $6.2 \times 10^{-6}$ moles) was added to a glass vial containing a Teflon coated magnetic stirbar. Copper(II) acetate (20 mg, $1.1 \times 10^{-4}$ moles) was also added along with 2 mL of benzene containing acetic acid at a 10% by weight concentration. The vial was placed inside a pressure reactor where the system was purged with nitrogen, and then filled with 80 psig (about 5 atm) of oxygen, and then filled to 300 psig (about 21 atm) with ethylene. The mixture was stirred and heated to 200° C. for 1 hour, after which the reactor was cooled and vented. The solution, which was originally a blue-slurry, remained blue following the reaction. The solution was centrifuged and analyzed by gas chromatography. The solution contained (117 mM, $2.3 \times 10^{-4}$ moles of styrene and 12 mM of vinyl acetate).

Example 4

Formation of Styrene from Benzene and Ethylene Using Rhodium(III) Acetylacetonate, Rhodium(III) and Palladium(II)

Syntheses were carried out in a 125 $cm^3$ stainless steel Parr pressure vessel. An insert was constructed so that up to six separate syntheses could be conducted under identical operation conditions (temperature, time, pressure). A typical synthesis consisted of adding 2 to 3 mg of catalyst (Rh(acac)$_2$Cl(H$_2$O), RhCl$_3$(H$_2$O)$_3$, or Pd(CH$_3$COO)$_2$) and 400 mg Cu(CH$_3$COO)$_2$ to a 5 mL glass vial equipped with a Teflon stirbar. 2 mL of benzene or a mixture of benzene and acetic acid (90/10 (v/v) or 50/50 (v/v)) was also added to the vial. A Teflon cap with a weep hole covered the vial. The vials were added to the Parr vessel, which was sealed, degassed, and pressurized with 300 psig (about 21 atm) of ethylene. In reactions for which the solvents contained acetic acid, the amount of Cu(CH$_3$COO)$_2$ was reduced to 20 to 30 mg, and the reactions were run under a mixture of 75/25 (p/p) of ethylene and oxygen with a total pressure of 300 psig (about 21 atm). The reactor was heated via an external oil bath and stirred with a magnetic stir motor. The reaction temperatures ranged from 150 to 200° C. and reaction times varied from 20 to 60 minutes. Following reaction, the reactor was cooled and slowly vented. An internal standard (chlorobenzene) was added to each vial and the mixture was analyzed by gas-chromatography for styrene, vinyl acetate, divinyl benzene, and stilbene.

TABLE 1

Comparison of Rh(acac)$_2$Cl(H$_2$O) and RhCl$_3$(H$_2$O)$_3$

| Catalyst | [Rh] (mM) | [Cu(OAc)] (mM) | Temp (° C.) | Solvent | Rxn Time (s) | [VA] (mM) | [STY] (mM) | TOF (s$^{-1}$) |
|---|---|---|---|---|---|---|---|---|
| Rh-acac | 5.5 | 1100 | 200 | S1 | 3720 | 6 | 114 | 5.6 × 10$^{-3}$ |
| Rh | 8.3 | 1100 | 200 | S1 | 3720 | 2 | 8 | 2.6 × 10$^{-4}$ |
| Rh-acac | 8.3 | 1100 | 220 | S1 | 2400 | 25 | 200 | 1.0 × 10$^{-2}$ |
| Rh | 10.0 | 1100 | 220 | S1 | 2400 | 5 | 17 | 7.1 × 10$^{-4}$ |
| Rh-acac | 3.1 | 62* | 200 | S2 | 3600 | 15 | 71 | 6.4 × 10$^{-3}$ |
| Rh | 3.8 | 61* | 200 | S2 | 3600 | 2 | 34 | 2.5 × 10$^{-3}$ |
| Rh-acac | 3.1 | 59* | 220 | S2 | 3000 | 12 | 117 | 1.2 × 10$^{-2}$ |
| Rh | 4.2 | 61* | 220 | S2 | 3000 | 8 | 79 | 6.3 × 10$^{-3}$ |
| Pd | 8.2 | 72* | 180 | S3 | 2280 | 388 | 155 | 1.6 × 10$^{-2}$ |
| Rh-acac | 3.1 | 65* | 200 | S3 | 3600 | 35 | 44 | 3.9 × 10$^{-3}$ |
| Rh | 4.2 | 61* | 200 | S3 | 3600 | 24 | 33 | 2.2 × 10$^{-3}$ |
| Rh-acac | 3.2 | 63* | 220 | S3 | 3000 | 37 | 72 | 7.5 × 10$^{-3}$ |
| Rh | 4.4 | 60* | 220 | S3 | 3000 | 23 | 60 | 4.5 × 10$^{-3}$ |

Rh-acac = Rh(acac)$_2$Cl(H$_2$O).
Rh = RhCl$_3$(H$_2$O)$_3$.
Pd = Pd(CH$_3$COO)$_2$
VA = vinyl acetate.
STY = styrene.
TOF = rhodium styrene turn-over frequency to styrene.
S1 = benzene.
S2 = 90/10 (v/v) benzene/acetic acid.
S3 = 50/50 (v/v) benzene/acetic acid.
* = reactions carried out using 75/25 (p/p) ethylene/oxygen.

As can be seen from the above data, use of the rhodium (III) acetylacetonate catalyst in the absence of acetic acid yielded catalyst turn over frequencies (5.6×10$^{-3}$ and 1.0× 10$^{-2}$) which are comparable to that obtained for the conventional prior art palladium(II) acetate catalyst (1.6×10$^{-2}$). Also, use of the rhodium(III) acetylacetonate catalyst in the absence of acetic acid yielded catalyst turn over frequencies (5.6×10$^{-3}$ and 1.0×10$^{-2}$) which are from about 10 to 20 times greater than that for the simple rhodium(III) catalyst, RhCl$_3$(H$_2$O)$_3$.

More importantly, the rhodium(III) acetylacetonate catalyst yielded a styrene to vinyl acetate ratio of from about 8 to about 20, as compared to a styrene to vinyl acetate ratio of about 0.5 for the conventional prior art palladium(II) acetate catalyst.

The practical catalyst turn over frequencies combined with the greatly improved selectively demonstrate that the rhodium(III) acetylacetonate catalyst offers a substantial advance over the conventional prior art palladium catalysts.

What is claimed is:

1. A process for coupling of an olefinic compound having at least one carbon—carbon double bond and at least one hydrogen atom attached to one of the carbon atoms of said carbon—carbon double bond, and an aromatic compound having aromatic ring atoms and a hydrogen atom covalently attached to at least one of said aromatic ring atoms, which process comprises the step of: reacting said olefinic compound with said aromatic compound in the presence of a rhodium(III) acetylacetonate catalyst and a copper(II) redox agent in a reaction medium which does not comprise a carboxylic acid component.

2. The process according to claim 1, wherein said rhodium (III) acctylacetonate catalyst is Rh(acac)$_2$Cl(H$_2$O).

3. The process according to claim 2, wherein said copper (II) redox agent is Cu(CH$_3$COO)$_2$.

4. The process according to claim 1, wherein said olefinic compound has from 2 to 12 carbon atoms, and has from zero to two substituents selected from the group consisting of: $C_{1-4}$ alkyl, $C_{3-6}$ cycloalkyl, $C_{6-12}$ aryl, $C_{7-16}$ alkaryl and $C_{7-16}$ aralkyl, wherein each of said substituents may be unsubstituted or may be further substituted with one or more substituents selected from the group consisting of: hydroxy, carboxylic acid, ester, aldehyde, ketone, amide, substituted amide, and nitro.

5. The process according to claim 2, wherein said olefinic compound has from 2 to 12 carbon atoms, and has from zero to two substituents selected from the group consisting of: $C_{1-4}$ alkyl, $C_{3-6}$ cycloalkyl, $C_{6-12}$ aryl, $C_{7-16}$ alkaryl and $C_{7-16}$ aralkyl, wherein each of said substituents may be unsubstituted or may be further substituted with one or more substituents selected from the group consisting of: hydroxy, carboxylic acid, ester, aldehyde, ketone, amide, substituted amide, and nitro.

6. The process according to claim 3, wherein said olefinic compound has from 2 to 12 carbon atoms, and has from zero to two substituents selected from the group consisting of:

$C_{1-4}$ alkyl, $C_{3-6}$ cycloalkyl, $C_{6-12}$ aryl, $C_{7-16}$ alkaryl and $C_{7-16}$ aralkyl, wherein each of said substituents may be unsubstituted or may be further substituted with one or more substituents selected from the group consisting of: hydroxy, carboxylic acid, ester, aldehyde, ketone, amide, substituted amide, and nitro.

7. The process according to claim 1, wherein said olefinic compound is ethylene.

8. The process according to claim 2, wherein said olefinic compound is ethylene.

9. The process according to claim 3, wherein said olefinic compound is ethylene.

10. The process according to claim 1, wherein said aromatic compound has from 6 to 12 carbon atoms, and has from zero to two substituents selected from the group consisting of: $C_{1-4}$ alkyl, $C_{3-6}$ cycloalkyl, $C_{6-12}$ aryl, $C_{7-16}$ alkaryl and $C_{7-16}$ aralkyl, wherein each of said substituents may be unsubstituted or may be further substituted with one or more substituents selected from the group consisting of: hydroxy, carboxylic acid, ester, aldehyde, ketone, amide, substituted amide, and nitro.

11. The process according to claim 2, wherein said aromatic compound has from 6 to 12 carbon atoms, and has from zero to two substituents selected from the group consisting of: $C_{1-4}$ alkyl, $C_{3-6}$ cycloalkyl, $C_{6-12}$ aryl, $C_{7-16}$ alkaryl and $C_{7-16}$ aralkyl, wherein each of said substituents may be unsubstituted or may be further substituted with one or more substituents selected from the group consisting of: hydroxy, carboxylic acid, ester, aldehyde, ketone, amide, substituted amide, and nitro.

12. The process according to claim 3, wherein said aromatic compound has from 6 to 12 carbon atoms, and has from zero to two substituents selected from the group consisting of: $C_{1-4}$ alkyl, $C_{3-6}$ cycloalkyl, $C_{6-12}$ aryl, $C_{7-16}$ alkaryl and $C_{7-16}$ aralkyl, wherein each of said substituents may be unsubstituted or may be further substituted with one or more substituents selected from the group consisting of: hydroxy, carboxylic acid, ester, aldehyde, ketone, amide, substituted amide, and nitro.

13. The process according to claim 9, wherein said aromatic compound has from 6 to 12 carbon atoms, and has from zero to two substituents selected from the group consisting of: $C_{1-4}$ alkyl, $C_{3-6}$ cycloalkyl, $C_{6-12}$ aryl, $C_{7-16}$ alkaryl and $C_{7-16}$ aralkyl, wherein each of said substituents may be unsubstituted or may be further substituted with one or more substituents selected from the group consisting of: hydroxy, carboxylic acid, ester, aldehyde, ketone, amide, substituted amide, and nitro.

14. The process according to claim 1, wherein said aromatic compound is benzene.

15. The process according to claim 2, wherein said aromatic compound is benzene.

16. The process according to claim 3, wherein said aromatic compound is benzene.

17. The process according to claim 9, wherein said aromatic compound is benzene.

18. The process according to claim 13, wherein said aromatic compound is benzene.

19. The process according to claim 3, wherein said aromatic compound is also said reaction medium.

20. The process according to claim 9, wherein said aromatic compound is also said reaction medium.

21. The process according to claim 17, wherein said aromatic compound is also said reaction medium.

22. The process according to claim 17, wherein said reaction is carried out at a temperature of about 150° C. to about 225° C.

23. The process according to claim 21, wherein said reaction is carried out at a temperature of about 150° C. to about 225° C.

24. The process according to claim 1, wherein said rhodium(III) acetylacetonate catalyst comprises a rhodium (III) acetylacetonate catalyst having one acetylacetonate group.

25. The process according to claim 1, wherein said rhodium(III) acetylacetonate catalyst comprises a rhodium (III) acetylacetonate catalyst having two acetylacetonate groups.

26. The process according to claim 1, wherein said rhodium(III) acetylacetonate catalyst comprises a rhodium (III) acetylacetonate catalyst having at least one halide atom.

27. The process according to claim 1, wherein said rhodium(II) acetylacetonate catalyst comprises a rhodium (III) acetylacetonate catalyst having two acetylacetonate groups and a halide atom.

28. The process according to claim 1, wherein the copper (II) redox agent comprises a compound having one copper atom.

29. The process according to claim 1, wherein the copper (II) redox agent comprises a copper(II) salt.

30. The process according to claim 25, wherein the copper(II) redox agent comprises a copper(II) salt.

31. The process according to claim 26, wherein the copper(II) redox agent comprises a copper(II) salt.

32. The process according to claim 27, wherein the copper(II) redox agent comprises a copper(II) salt.

33. The process according to claim 1, wherein the copper (II) redox agent comprises an inorganic copper(II) salt.

34. The process according to claim 1, wherein the copper (II) redox agent comprises an organic copper(II) salt.

35. The process according to claim 25, wherein the copper(II) redox agent comprises an organic copper(II) salt.

36. The process according to claim 26, wherein the copper(II) redox agent comprises an organic copper(II) salt.

37. The process according to claim 27, wherein the copper(II) redox agent comprises an organic copper(II) salt.

* * * * *

UNITED STATES PATENT AND TRADEMARK OFFICE
CERTIFICATE OF CORRECTION

PATENT NO.   : 6,127,590
DATED        : October 3, 2000
INVENTOR(S)  : Douglas Taube et al.

It is certified that error appears in the above-identified patent and that said Letters Patent is hereby corrected as shown below:

Claim 2, column 14,
Line 16, replace "acctylacetonate" with -- acetylacetonate --.

Claim 27, column 16,
Line 29, replace "rhodium(II)" with -- rhodium(III) --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*